(12) United States Patent
Iba

(10) Patent No.: US 6,186,781 B1
(45) Date of Patent: Feb. 13, 2001

(54) SURVEYOR FOR FALSE TOOTH DESIGN

(76) Inventor: Nobuyuki Iba, 63-6, Minami-ochiai, Makishima-cho, Uji-shi, Kyoto 611 (JP)

( * ) Notice: Under 35 U.S.C. 154(b), the term of this patent shall be extended for 0 days.

(21) Appl. No.: 09/284,602
(22) PCT Filed: Sep. 8, 1997
(86) PCT No.: PCT/JP97/03171
  § 371 Date: Apr. 19, 1999
  § 102(e) Date: Apr. 19, 1999
(87) PCT Pub. No.: WO99/12493
  PCT Pub. Date: Mar. 18, 1999
(51) Int. Cl.$^7$ .................................................... A61C 3/00
(52) U.S. Cl. ................................... 433/50; 433/55; 433/60
(58) Field of Search .................................. 433/50, 55, 56, 433/60, 75

(56) References Cited

U.S. PATENT DOCUMENTS

| | | | |
|---|---|---|---|
| 1,598,535 | * 8/1926 | Lentz | 433/56 |
| 2,376,384 | * 5/1945 | Ringle et al. | 433/50 |
| 3,150,448 | * 9/1964 | Wozar | 433/50 |
| 4,205,445 | 6/1980 | Tzeng | 433/50 |
| 5,660,544 | * 8/1997 | Shih | 433/55 |

FOREIGN PATENT DOCUMENTS

| | | |
|---|---|---|
| 55-19197 | 2/1980 | (JP). |
| 59-84108 | 5/1984 | (JP). |
| 60-163654 | 8/1985 | (JP). |
| 6-292694 | 10/1994 | (JP). |
| 7-47089 | 2/1995 | (JP). |

* cited by examiner

*Primary Examiner*—John J. Wilson
(74) *Attorney, Agent, or Firm*—Armstrong, Westerman, Hattori, McLeland & Naughton

(57) ABSTRACT

This is the apparatus that designs the denture and enable to process complehensively both of the clasp designing and the base designing, and designs the denture which can be inserted smoothly and has the suitable resistant force against taking-off and the bracing force after insertion.

This is the apparatus that contains the surveyor table (2) to set the dental plaster cast M and the survey line drawing means (3) to draw the survey line for the clasp and the base on the cast, and survey table contains the dental plaster setting means (10) which is able to move and fix individually around the each axis through the base table, the first axle (PA-1) extending parallel on the base table and the second axle (PA-2) extending vertically at the cross point, the Z axis center adjustment mechanism (11), the universal joint mechanism (12) and the fine angle adjustment mechanism (100), the survey line drawing device contains the drawing shaft (57) extending vertically and enable to move the drawing shaft separatelly toward the X axis and the Y axis direction and to lock individually.

7 Claims, 13 Drawing Sheets

Fig.9
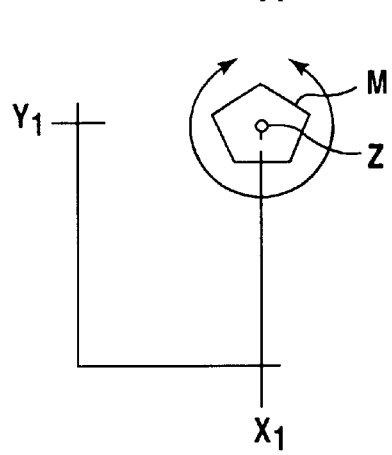
A
$Y_1 - X_1 - Z - U - M$
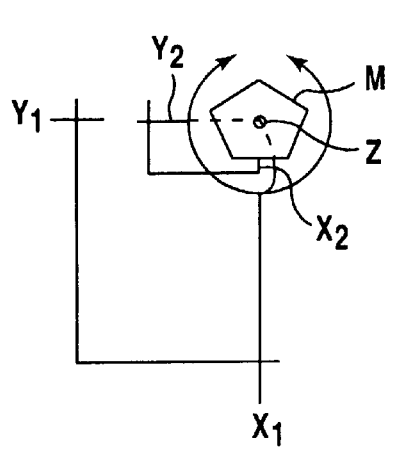
B
$Y_1 - X_1 - Z - Y_2 - X_2 - U - M$
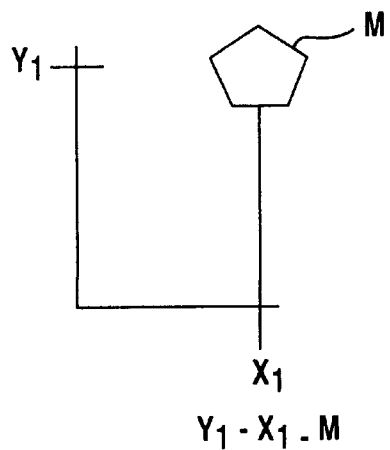
C  PRIOR ART
$Y_1 - X_1 - M$

SURVEYOR FOR FALSE TOOTH DESIGN

TECHNICAL FIELD

This invention relates to the mechanical-tool used for dental-technology, especially relates to the surveyor apparatus used for the denture designings. Using this apparatus, it enable to process comprehensively both of the clasp designing and the base designing, accordingly the produced denture is easily inserted into the mouth and gives a suitable resistant force against taking-off and the bracing after insertion.

BACKGROUND ART

As is known in the dental treatment, for example, in the case that teeth are missed or damaged, the denture is often set for the patient. At first, the dentist make an oral impression-taking of the mouth and then accordingly the dental plaster cast is produced. This cast is completely reproduced of the patient mouth: soft tissue(gingiva), healthy remaining teeth standing from the gingiva and edentulous areas made by damage or injury. Using this plaster cast, for example, the denture is made for the edentulous areas of the patient.

The above mentioned denture, for example showed in FIG. 8 (in the case of wire-clasps), is consist from the artificial teeth (FT) and the denture base (RF). This type of denture is produced to hold the adjacent healthy remaining teeth (named clasped tooth : ST) by using clasp C, for example, wire-clasp or cast-clasp to get the resistant force against removing. For the denture, it is very important to design the clasps and the denture base for smooth and natural setting.

The above mentioned clasp used in the dental treatment is mainly devided into the wire-clasp which is, for example, made by bending the ready-made metal wire of a diameter about 1 mm and the cast-clasp which is made by casting the wax pattern, for example, with Co—Cr alloy, Pt—Au alloy, Au alloy, Pd alloy and so on.

Showing in FIG. 8B and FIG. 8C, for example, clasp C is consisted from the curved portion AP (called the clasp arm portion AP) which is fitted to the undercut surface of adjacent healthy remaining teeth ST and the leg-portion LP which is bedded into resin base RF.

As you make denture, it is important to design the denture-base and clasps. This designing is to draw the outline of the denture-base and clasps composed the denture on the dental plaster cast. When you design clasps, if you don't make a enough observation of the tooth contour, the produced denture has verious troubles caused from the amount of undercut: for example, difficult to insert into the mouth, or not enough resistant force against removing and bracing after setting brings to take out too easy. Therefore, in designing the clasps and the denture-base, drawing of the outline of clasps on the dental plaster cast is very important and accordingly gives the great effect to the efficiency for denture producing processes and decides the quality of denture.

In the usual designing method of the denture, the usual surveyor apparatus which is representative of the NEY surveyor apparatus is used. This usual type of surveyor apparatus is composed with the surveyor table which can adjust and fix the direction of denture designing for the dental plaster cast and the survey line drawing device which holds the drawing lead material vertically. The methods of survey line drawing with the usual surveyor are following:

First, the dental plaster cast is fixed on the surveyor table and the path of insertion of the denture is decided. Then shown in the FIG. 14A and FIG. 14B, the survey line 80 (survey line is the line connecting the greatest circumference of tooth or tissue which is drawn on the cast by using the vertical drawing shaft like a pencil lead. It is called the survey line A which is drawn as the reference line to know the undercut area for the direction of designing. And it is called the survey line B which is drawn to get the outline of the clasp by tilting the Y axis and the X axis for the direction of designing. And It is called the survey line K which is drawn to get the outline of the base by tilting the X axis and the Y axis. After now, it is called separately the survey line A,B and K.) is drawn on the dental plaster cast with the survey line drawing tool (In this case, the line is called the survey line A.). And using the undercut guage, amounts of undercut is measured according to the elasticity of clasp-material the clasp, and the measured point V is decided as the terminal portion of clasp. Then, for the clasp arm portion AP, the outline is drawn by hand depending on the empirical knowledge and intuition. The outline of the denture base is also drawn in the same way.

Usually, in designing the Akers-type clasp, as shown in FIG. 14A for the case of wire-clasp, ⅔ of the opening terminal side of the clasp arm is designed to set into the undercut area. However, the denture produced in this way has problems functionally in the mouth, for example, low stability against the horizontal movement and less-resistance against for the lift-up movement of the prosthetic side. These problems are caused from the reason that the curved arm portion AP of clasp C affects holding effect for the clasped tooth ST mainly only with the terminal portion of clasp. This problem is not solved by using bigger undercut amount and deciding the measured point V'. It is necessary to design the clasp with longer undercut portion and holding the clasped tooth ST as shown in FIG. 14B, and get a high resistant force against the various working directions.

In the case of wire-clasp shown in FIG. 14B, the method which the clasp arm is inserted into undercut portion from the less-elastic portion near the clasp body to the clasp tip is introduced as "YAZAKI clasp" in the book of "Wire-Clasp" by Seiji Kawabe, but in this method, the outline of clasp is drawn depending on the empirical knowledge and intuition, so the resistant force of each clasps may not be uniform and sometime happen the problem which can not be inserted for the reason of tightness. In the new designing method of introducing now, the clasp arm is also inserted into undercut area from the portion near the clasp body like as YAZAKI clasp, but the survey line B is drawn using surveyor (83' in FIG. 7) and this survey line B is used for designing the outline of clasp. By making a rule of drawing the survey line, it is possible to design the clasp which has uniform resistant force and is easy to insert for any kinds of cases.

About this invention, one more invention of the surveyor apparatus for clasp designing is known in Japanese Laid-Open Patent Publication No.47,089 of 1995 (official report) invented by the same person (called the formar invention). This former invented apparatus has the structure being able to drow the survey line B by rotating two axis of the X and the Y and giving the inclination to the cast, but this time new improvement is added. In the clasp designing surveyor apparatus of the former invention, the surveyor table is controlled only with the two rotary axis of X-axis and Y-axis, and it has the problem to happen errors for the angle setting when either of the X-axis or Y-axis is inclined.

Then, it is mentioned about the improvement of the structure to dissolve the angle setting error happened in the former invention. As shown in FIG. 9C, in the former invention, the relation of the rotary axis and the cast is consisted with the Y1-axis, the X1-axis and the dental plaster cast setting device. On the other hand, in this invention, as shown in FIG. 9A, the first component has the relation of the Y1 axis, the X1 axis, the Z axis, the universal joint mechanism and the dental plaster cast setting device. As shown in FIG. 9B, the second component has the relation of the Y1 axis, the X1 axis, the Z axis, the Y2 axis, the X2 axis, the universal joint mechanism and the dental plaster cast setting device.

The new surveyor apparatus is composed with the axis which has the rotary axis of the Z axis extending vertically at the cross point of the rotary axis of the X1 axis and the Y1 axis, the X2 axis and the Y2 axis which is extended vertically for the Z rotary axis and is the same direction for the X1 axis and the Y1 axis, the universal joint which is extended vertically at the cross point of the rotary axis of the X2 axis and the Y2 axis, and the dental plaster cast setting plate which is on the universal joint.

Then, in this designing method for the denture, the items needed for angle setting is listed.
(a) the angle setting for the direction of the basic designing.
(b) the angle setting for the clasp designing.
(c) the angle setting for the denture base designing.

In the former invention, the above three angle setting is made with only the Y1 axis and the X1 axis, therefore the angle error happens when the additional angle setting is needed with the inclined axis of either the X axis or the Y axis after the first angle setting.

And in the former invention, above (c) item is not mentioned. In this invention, each needed angle setting is able to do independently. And more, the angle setting for the denture base designing is newly proposed.

The main role of each axis of this invention is mentioned (shown in FIG. 9 and FIG. 10).
(a) The angle setting for basic designing direction setting.
   It is setted with the universal joint mechanism 12.
(b) The angle setting for clasp designing.
   It is setted with the X1 axis, the Y1 axis and the Z axis, or with the X2 axis, the Y2 axis and the Z axis,
(c) The angle setting for denture base designing.
   It is setted with the X1 axis, the Y1 axis and the Z axis, or with the X2 axis, the Y2 axis and the Z axis.

This inventional apparatus do not happen the error when the designing for the denture base and the clasp is made separately after the basical designing direction setting, it is differ from the former invention. So, this surveyor apparatus is able to design the denture which is aesthetic and has clasps with suitable resistant force for verious working direction.

Untill now the designing direction for the denture base and the clasp is made only with the same direction, but in this invention shown in FIG. 15, the situation untill the clasp arm AP reach to touch to the surface of the clasped tooth is considered as the designing direction E of the denture base, and the situation after that till the denture is inserted on the mucous membrane is considered as the designing direction F of the clasp. By this designing method that the designing direction of the clasp and the base are divided individually, it is possible to design the denture which the denture base and the bar are bedded into the deep undercut area shown in FIG. 13.

Further, this invention provides the surveyor apparatus which the pencil shaft for the survey line drawing device (shown in FIG. 6 and FIG. 12) is removable type and enable to sharpen the pencil rod quickly and enable to change easily the drawing holder with another color pencil rod or measuring rod, so brings higher working efficiency.

DISCLOSURE OF THE INVENTION

To obtain the above-mentioned purpose, this invention designing that is composes the surveyor apparatus for the denture designing that is composed with the surveyor table on which the dental plaster cast is mounted and the survey line drawing means to draw the survey line for the denture base and clasps on the cast,
   said surveyor table including, the base table,
   the dental plaster cast setting means which is connected to be able to move and fix individually around for each axle through the first axles which is parallel to said base table, the second axle which crosses at right angle to the first axle, and the third axle which is stand vertically at the cross point of said first and second axle,
   the first angle-adjustment mechanism which can rotate the dental plaster cast setting means around the first axle and fix to the desired angle,
   the second angle-adjustment mechanism which can rotate said dental plaster cast setting means around the second axle and fix to the desired angle,
   the third angle-adjustment mechanism which can rotate said dental plaster cast setting means around the third axle and fix to the desired rotary angle,
   the Z-axis center adjustment mechanism which is positioned between said dental plaster cast setting means and said third axle and adjusts the working origin of the working cast mounted on the dental plaster cast setting means to the axis center of the third axle, and
   the universal joint which is able to set the standard plane of the working cast to the desired angle against the horizontal plane.

And this invention composes the denture designing surveyor apparatus that contains the surveyor table to set the dental plaster cast, the drawing device to draw the survey line for the denture base and clasps on the cast,
   said surveyor table including, the base table,
   the dental plaster cast setting means which is connected to be able to move and fix individually around for each axle through the first axles which is parallel to said base table, the second axle which crosses at right angle to the first axle, and the third axle which is stand vertically at the cross point of said first and second axle,
   the first angle-adjustment mechanism which can rotate the dental plaster cast setting means around the first axle and fix to the desired angle,
   the second angle-adjustment mechanism which can rotate said dental plaster cast setting means around the second axle and fix to the desired angle,
   the third angle-adjustment mechanism which can rotate said dental plaster cast setting means around the third axle and fix to the desired rotary angle,
   the Z-axis center adjustment mechanism which is positioned between said dental plaster cast setting means and said third axle and adjusts the working origin of the working cast mounted on the dental plaster cast setting means to the axis center of the third axle,
   the universal joint which is able to set the standard plane of the working cast to the desired angle against the horizontal plane, and
   the fine angle adjustment means which has the individually each axle said first axle and said second axle between said Z axis center adjustment mechanism and the universal joint mechanism.

BRIEF DESCRIPTION OF THE DRAWINGS

FIG. 9 is the outline which shows the principle of each structure comparing the surveyor apparatus with the first structure and the surveyor apparatus with the second structure. FIG. 9A is the principle figure of the surveyor apparatus with the first structure and shows the structure composed with the Y1 axis, the X1 axis, the Z axis, the universal joint mechanism and the dental plaster cast setting device. FIG. 9B is the principle figure of the surveyor apparatus with the second structure and shows the structure composed with the Y1 axis, the X1 axis, the Z axis, the Y2 axis, the X2 axis, the universal joint mechanism and the dental plaster cast setting device. FIG. 9C is the principle figure of the surveyor apparatus with usual two axis structure (the Y1 axis, the X1 axis and the dental plaster cast setting device).

FIG. 14 is the figure that explains the method to draw the survey line 80 with the survey line drawing device and FIG. 14A is the outline of the side view which shows the case that insert the ⅔ of the opening side terminal of the clasp arm AP into undercut area in the usual Akers-type clasp designing and FIG. 14B is the outline of the side view which shows the case with longer undercut portion of clasp arm AP.

BEST MODE FOR EMBODYING THE INVENTION

About the first structure of this surveyor apparatus for designing the denture, the detail explanation is shown in figure according to the definite example.

Figure 1:
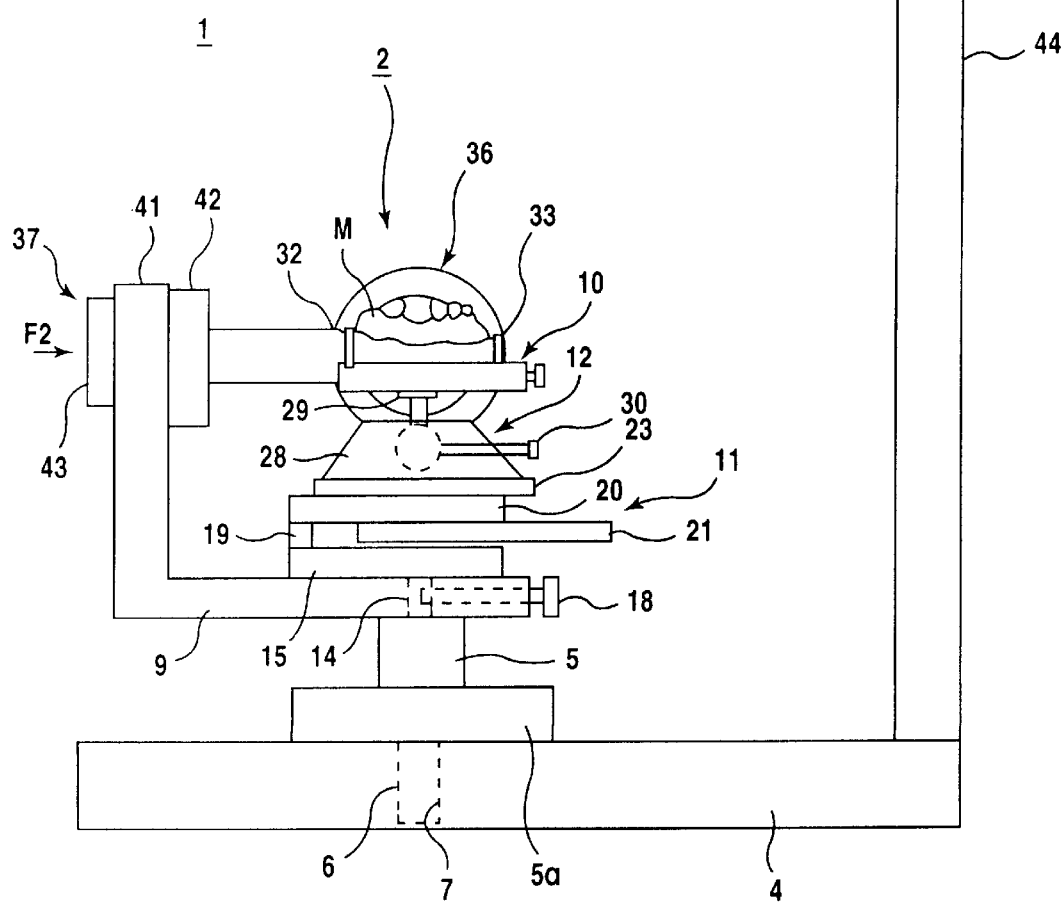
FIG. 1 is the outline of the definite side view of the first component of the denture designing surveyor apparatus in this invention.
Figure 2:
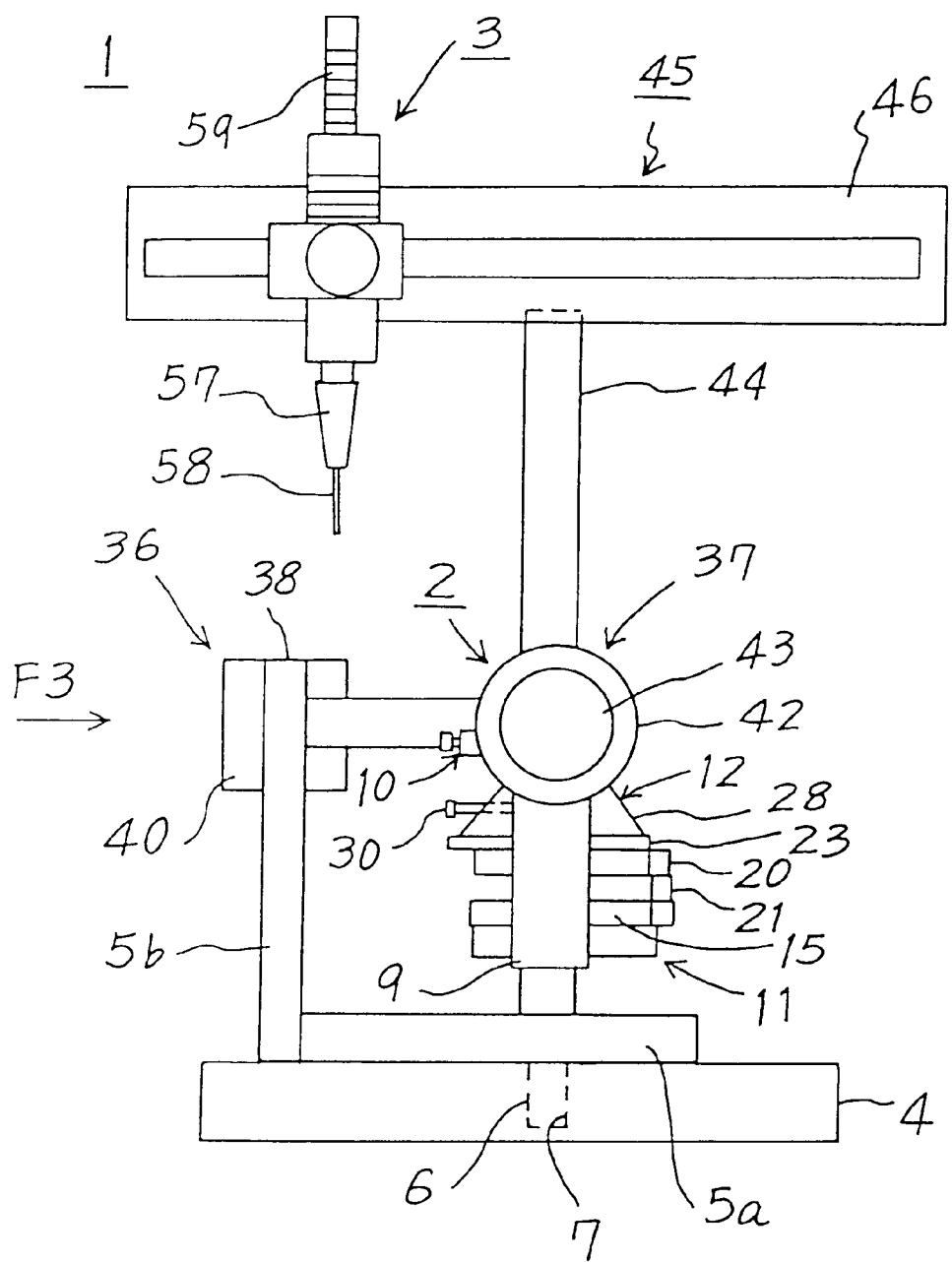
FIG. 2 is the outline of the side view of the same surveyor apparatus observed from the arrow F2 in FIG. 1.
Figure 3:
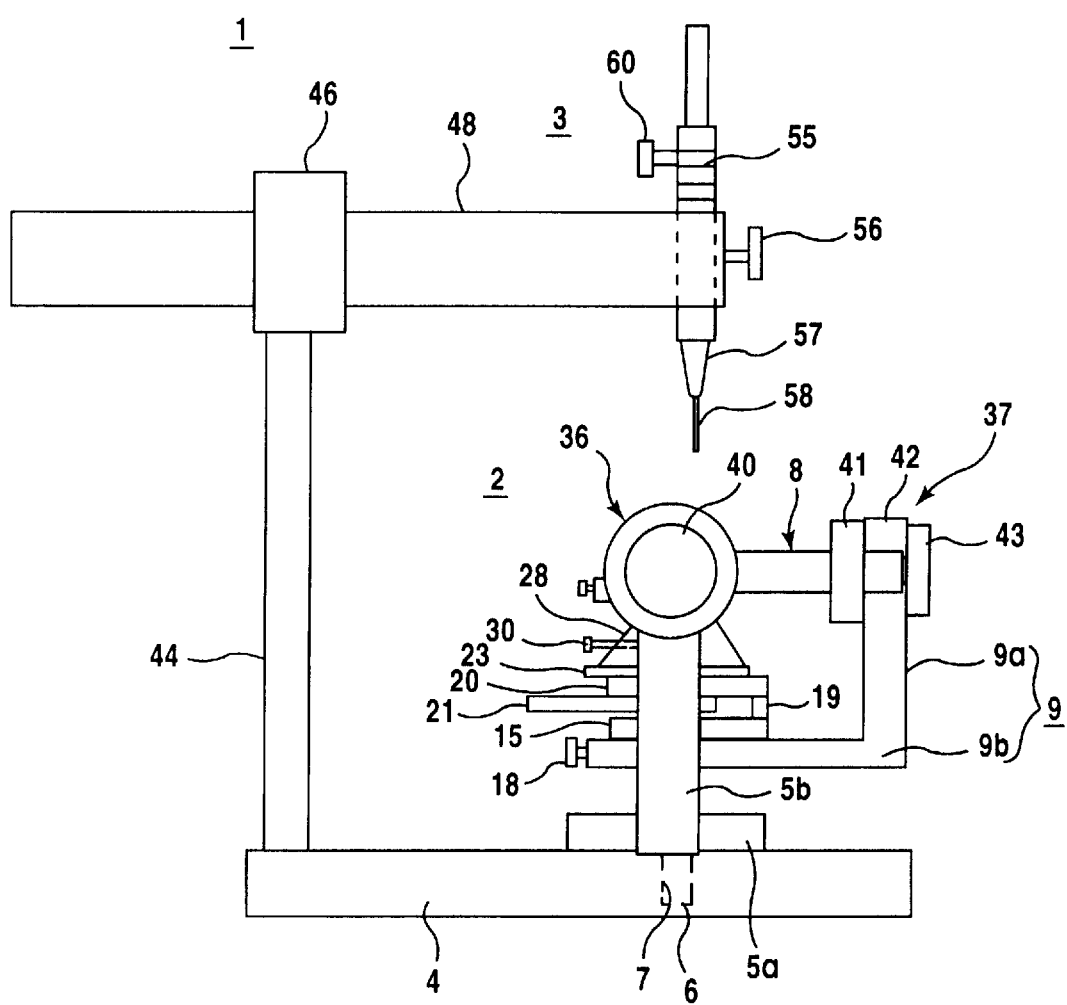
FIG. 3 is the outline of the side view of the same surveyor apparatus observed from the arrow F3 in FIG. 2.
Figure 4:
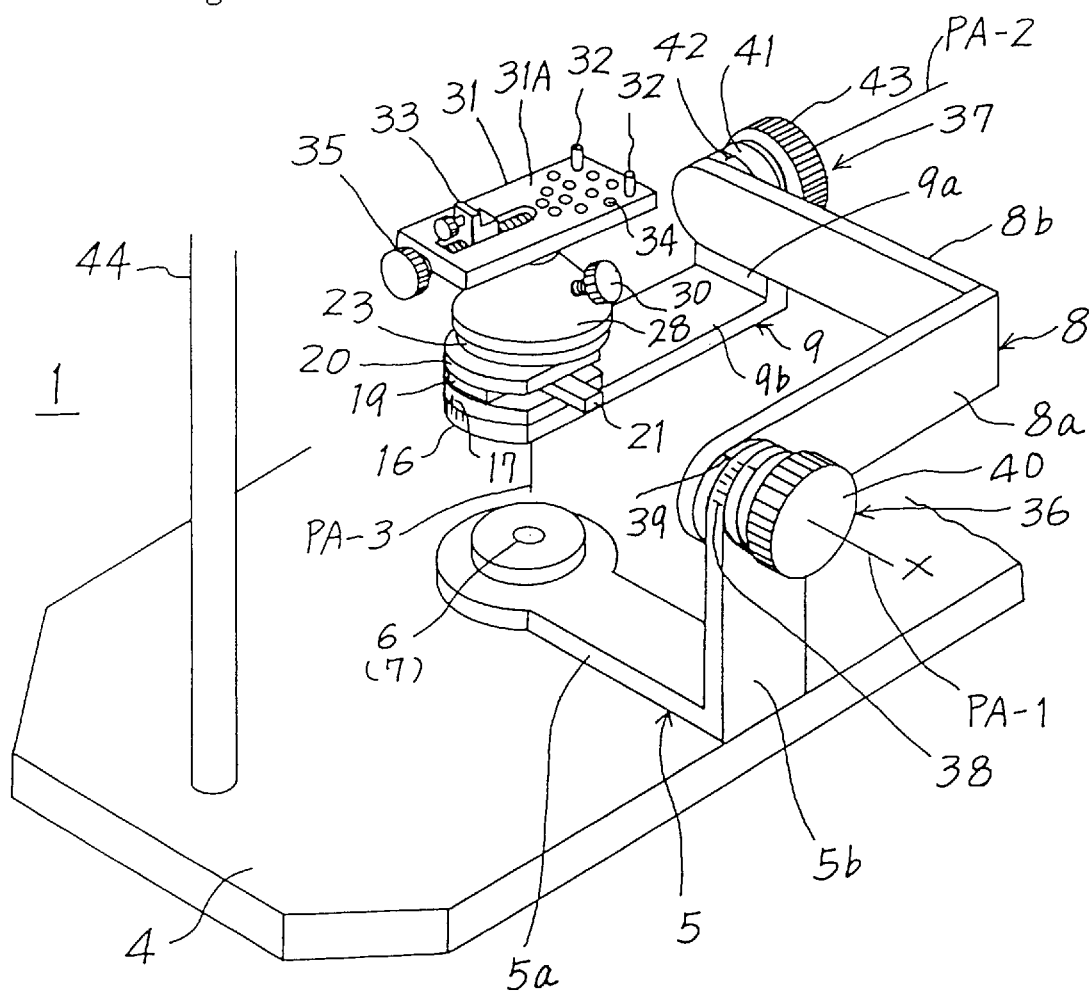
FIG. 4 is the outline of the squint view which shows to understand the basic structure of the surveyor table in the same surveyor apparatus.
Figure 5A:
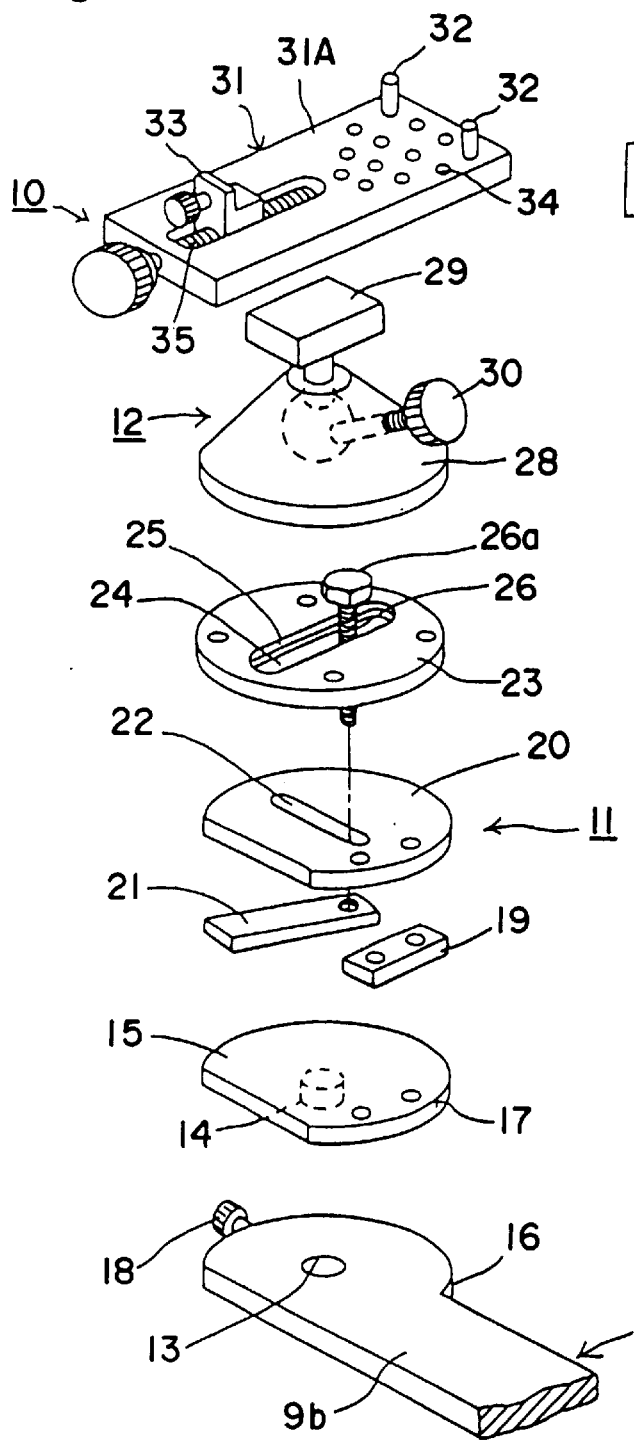
FIG. 5 is the outline of the squint view which shows to decompose the inner structure of the surveyor table in the same surveyor apparatus.
Figure 5B:
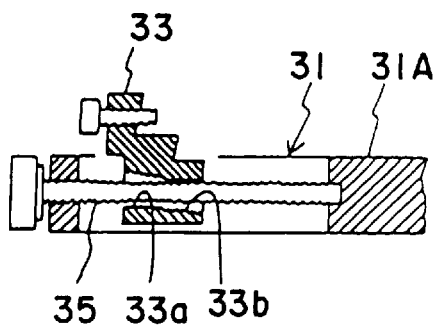
Figure 6:
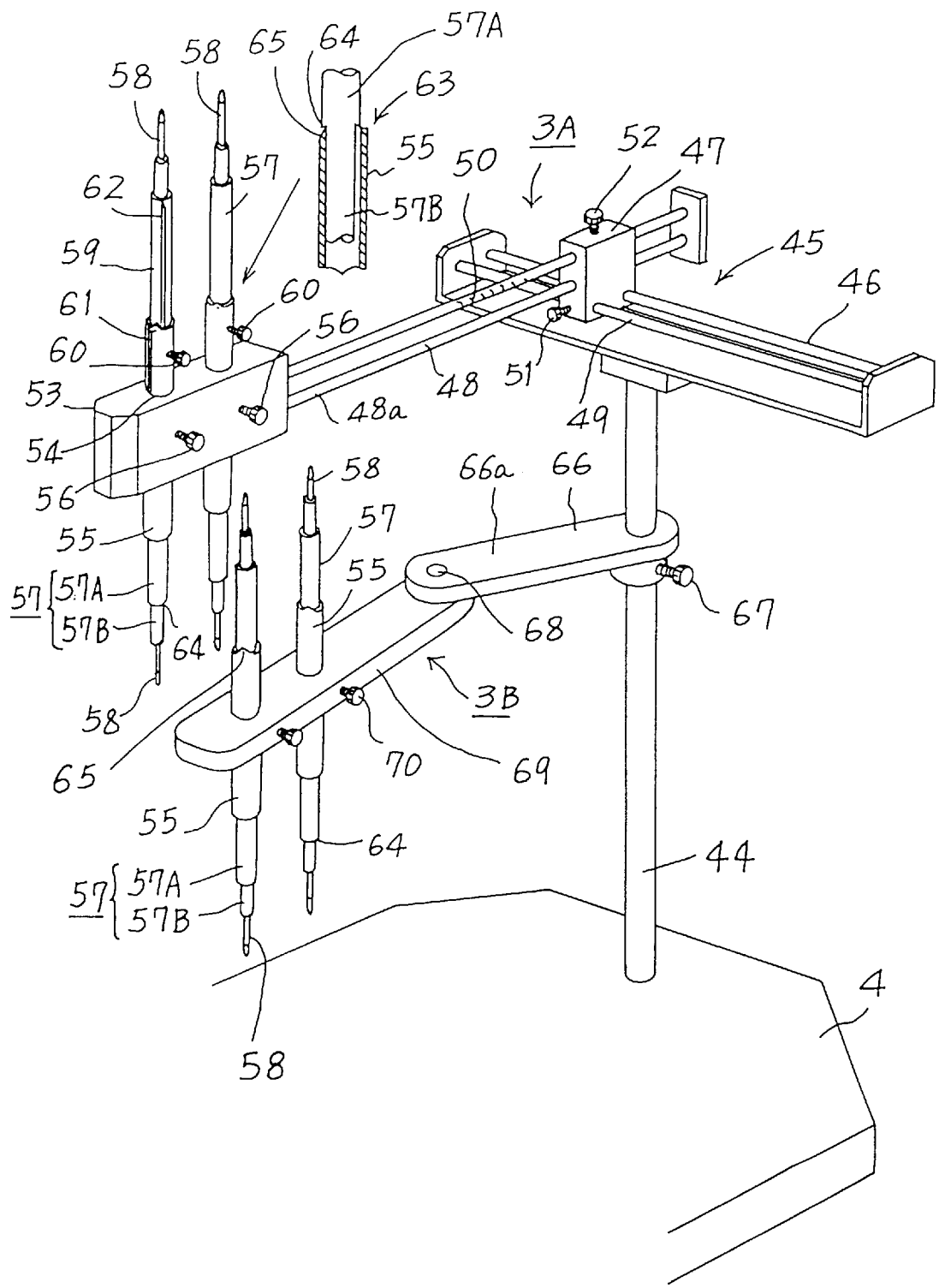
FIG. 6 is the outline of the squint view which shows the definite structure of the survey line drawing device in the same surveyor apparatus.

FIG. 1 is the definite example of the denture designing surveyor apparatus with the first structure of this invention and shows the side view of the total structure. FIG. 2 shows the side view of FIG. 1 from the arrow F2 direction. FIG. 3 shows the side view of FIG. 2 from the arrow F3 direction. And FIG. 4 is the squint view to show the basic structure of the surveyor table of this surveyor apparatus. FIG. 5 roughly shows the squint view of the decomposed surveyor table which shows the inner structure. FIG. 6 roughly shows the squint view of the definite example of the survey line drawing device.

In the case of the first structure shown in FIG. 1~FIG. 5, this invented surveyor apparatus 1 for designing the denture basically contains the surveyor table 2 for mounting the dental plaster cast M and the survey line drawing device 3 to draw the survey line 80, 83 on the dental plaster cast M.

The surveyor table 2 stands on the base table 4 and the prop member 5 is constructed to be able to rotate for the base table 4. In the enforced case shown in figure, the prop member 5 is constructed with the horizontal plate part 5a, the vertical plate part 5b which extends vertically from the one terminal of the horizontal plate part 5a and the rotary axis 6 under the other terminal of the horizontal plate part 5a, and this rotary axis 6 fits into the hole 7 at the center of the base table 4 to be able to rotate. It is the view point of working effect during the working that the prop member 5 can rotate around the rotary axis 6.

The base table 4 and the prop member 5 has the mechanism that can be locked at the position of each 90 degree with relation to the survey line drawing means 3 which is handled along the direction of X-axis and Y-axis.

This surveyor table 2 has the first axle PA-1 which is crossed with the prop member 5 and extends toward the X-axis direction at the upper side of the vertical plate part 5b of the prop member 5. The X-Y axis connecting arm member 8 is connected on the upper side of the vertical plate part 5b of the prop member 5 through the first axle PA-1 and capable to rotate and fix around the axle. The X-Y axis connecting arm member 8 is composed with the first plate part 8a and the second plate part 8b which extends to cross at right angle from the one terminal of the first plate part 8a, in the enforced case shown in figure.

This surveyor table 2 has the second axle PA-2 which crosses at right angle to the first axle PA-1 and extends toward the Y-axis direction at the one terminal of the second plate part 8b of the X-Y axis connecting arm member 8. The Y-Z axis connecting arm member 9 is connected to the one terminal of the second plate part 8b of the X-Y axis connecting arm member 8 through the second axle PA-2 and capable to rotate and fix around the axle. The Y-Z axis connecting arm member 9 is composed with the first plate part 9a and the second plate part 9b which extends to cross at right angle from the first plate part 9a in the enforced case shown in figure.

This surveyor table 2 has the third axle PA-3 at the one terminal of the second plate part 9b of Y-Z axis connecting arm member 9 that extends vertically toward the Z axis direction at the intersection point of the first axle PA-1 and the second axle PA-2.

The dental plaster cast setting means 10 is connected to be able to rotate and fix around the axle at the terminal side of the second plate part 9b of the Y-Z axis connecting arm member 9 through the third axle PA-3.

Between the dental plaster cast setting means 10 and the third axle PA-3, this invention has the Z axis adjustment mechanism 11 which adjusts the working origin CP (the central point of the area L in FIG. 7B) of the working cast M mounted on the dental plaster cast setting means 10 and the universal joint mechanism 12 which is able to adjust the working cast M to the any angle against the horizontal plane.

Now the definite example of the construction that fits the dental plaster cast setting means 10 on the second plate part 9b of the Y-Z axis connecting arm member 9 through the Z axis adjustment mechanism 11 and the universal joint mechanism 12 is explained in the enforced case shown in FIG. 5.

At the free end of the second plate part 9b of the Y-Z axis connecting arm member 9, the axis hole 13 is arranged. The Z axis rotary scale disk 15 has the axis portion 14 in the lower surface that is fitted to the axis hole 13 to be able to rotate and fix. The angle scale 16 is engraved on the one side of the free terminal round side surface of the second plate part 9b of the Y-Z axis connecting arm member 9, and the reference line 17 is engraved on the other side. The Z axis rotary scale disk 15 is possible to fix with the rotary fixing screw 18.

The disk 20 with oblong hole of the X(Y)-axis direction is fixed to the Z-axis rotary scale disk 15 through the connecting spacer member 19. The connecting spacer member 19 makes sure of movable space which arranges the Z axis point fixing handle 21 to rotate freely between the Z axis rotary scale disk 15 and the disk 20 with the oblong hole for the X(Y)-axis direction. The disk 20 with the oblong hole for the X(Y)-axis direction has the oblong hole 22 of the X(Y)-axis direction which is extended to the diameter direction through the center of the disk.

The disk 23 with the oblong hole of the X(Y)-axis direction is arranged to move freely each other on the upper surface of the disk 20 with the oblong hole for the X(Y)-axis direction. The disk 23 with the oblong hole of the X(Y)-axis direction has the oblong hole 24 of the X(Y)-axis direction which is extended for the diameter direction through the center of the disk, and more has the long groove 25 which is opened with the similar figures on the upper surface of the oblong hole 24 for the Y(X)-axis direction.

The disk 20 with the oblong hole for the X(Y)-axis direction and the disk 23 with the oblong hole for the Y(X)-axis direction are arranged to fix at the proper position of the X axis and the Y axis by the rotary operation of the Z axis point fixing handle 21 with the bolt 26 which goes through the oblong hole 24 of the Y(X)-axis direction of the disk 23 with the oblong hole of the Y(X)-axis direction and the oblong hole 22 of the X(Y)-axis direction of the disk 20 with the oblong hole of the X(Y)-axis direction and the Z axis point fixing handle 21 which has the screw hole to fit with the bolt 26 on the one terminal side. The six-angle head 26a of the bolt 26 is to be fitted into the long groove 25 and resists the rotation of the bolt 26.

The universal joint mechanism 12 is constructed with the base portion 28 which is fixed on the upper surface of the disk 23 with the oblong hole of the Y(X)-axis direction by the fixing means as the screw, the connecting member 29 which is arranged to move freely around the base portion 28 and the tightening screw part 30 which fix the free moving between the base portion 28 and the connecting member 29. The universal joint mechanism 12 is fixed by the tightening screw member 30 after deciding the designing direction of the cast M.

The dental plaster cast setting means 10 includes the dental plaster cast setting plate 31 which is fixed on the connecting member 29 of the universal joint mechanism 12. The dental plaster cast setting plate 31 has the setting support members 32 and 33 for fixing the dental plaster cast M on the upper side 31A. For example, the setting support member 32 is composed with the couple of pins and fixed by inserting into the plural holes 34 in the dental plaster cast setting plate 31.

The other setting support member 33 has the penetrated hole 33a with inclined screw hole portion 33b and is inserted into the tightening screw 35 through the penetrated hole 33a. The other setting support member 33 is able to move smoothly for the horizontal direction on the load-free situation shown in figure and is inclined on the load situation with setting cast and the inclined screw hole portion 33b is engaged with the tightening screw 35, and under this situation, the dental plaster cast M is to be fixed between the pair of the setting support part 32 and the other setting support member 33 by rotating process of the tightening screw 35.

By these combinations, the dental plaster cast M is mounted on the dental plaster cast setting means 10. In this invention, it is necessary to adjust the working origin CP of the dental plaster cast M to the third axle PA-3 that is the center of the Z axis. This adjustment is done by the Z axis adjustment mechanism 11. Moving properly the disk 20 with the oblong hole of the X(Y) axis direction and the disk 23 with the oblong hole of the Y(X) axis direction, the working origin CP of the dental plaster cast M is able to adjust and set to the center of the Z axis by tightening the Z axis point fixing handle 21 to the bolt 26 through the long hole 22 and 24 of each disk.

In this invention, the surveyor table 2 is composed with the first angle adjustment mechanism 36 related to the first axle PA-1 and the second angle adjustment mechanism 37 related to the second axle PA-2. The first angle adjustment mechanism 36 rotates the dental plaster cast setting means 10 around the first axle PA-1, that is the X axis, and is possible to fix the setting means 10 to the desired angle, and is composed with the X-axis rotary scale 38, the zero point setting gauge 39 and the tightening dial 40.

And the second angle adjustment mechanism 37 is to rotate the dental plaster cast setting means 10 around the second axle PA-2, that is the Y axis, and is possible to fix the setting means 10 to the desired angle, and is composed with the Y axis rotary scale 41, the zero point setting gauge 42 and the tightening dial 43.

On the other hand, shown in FIG. 6, the survey line drawing means 3 has the pole member 44 extending upward from the base table 4. The survey line drawing means 3 is composed with the two another kinds (3A and 3B) to use together, but it is enough for eighter of them. The first survey line drawing device 3A is basically composed with the mentioned later drawing shaft operating mechanism 45 which is possible to move the drawing shaft to the X-axis direction and the Y-axis direction individually and to fix individually.

The first survey line drawing means 3A is composed with the X-axis direction guide rail 46 attached to the pole member 44, the X-Y cross guide holder 47 which is combined with the X-axis direction guide rail 46 and is able to move along the guide rail 46 and the Y-axis direction guide rail 48 which is combined with the X-Y cross guide holder 47.

In the first survey line drawing means 3A, the X-axis direction guide rail 46 and the Y-axis direction guide rail 48 are composed at least with 2 bars each and they have the scale 49 and 50 that measures the moving length for the each axis direction.

In the first survey line drawing means 3A, the locking means 51 is arranged between the X-Y cross guide holder 47 and the X-axis direction guide rail 46, and the locking means 52 is arranged between the X-Y cross guide holder 47 and the Y axis direction guide rail 48, and they are able to lock individually.

The first survey line drawing means 3A has the cylinder holder 53 at the one terminal 48a of the Y-axis direction guide rail 48. The cylinder holder 53 has the plural vertical cylinder insertion holes 54 which is arranged to insert and hold the drawing shaft holding cylinder 55. The drawind shaft holding cylinder 55 is fixed to hold in the cylinder holder 53 by the cylinder ups and downs adjusting screw 56.

In this invention, the drawing shaft 57 is composed with, for example,the shaft part holding the pencil rod 58 for each side, and is held to insert into the drawing shaft holding cylinder 55. And the height adjusting scale 59 is arranged on the round surface of the drawing shaft 57. And the drawing shaft 57 is fixed to the the drawing shaft holding cylinder 55 by the height adjusting screw 60. The terminal of the pencil rod 58 is arranged about 75° with the pencil sharpner attached on the surveyor table.

The way that protects the rotation of the drawing shaft 57 in the drawing shaft holding cylinder 55 is arranged between the drawing shaft holding cylinder 55 and the drawing shaft 57. This mechanism is actually composed with the rotation protecting nob 61 extended along the inner round surface of the drawing shaft holding cylinder 55 toward the generating line and the rotation protecting groove 62 extended along the outer round surface of the drawing shaft 57 toward the generating line.

The drawing shaft holding cylinder 55 is able to fix each 90° angle against the cylinder holder 53 by the cylinder ups and downs adjusting screw 56.

Between the drawing shaft holding cylinder 55 and the drawing shaft 57, there is the hanging means 63 which holds the drawing shaft 57 by one touch to the non-working situation. This hanging means 63 has the large diameter portion 57A and the small diameter portion 57B, and the step seat of the large diameter portion 57A and the small diameter portion 57B is formed as the inclined step seat 64 and is composed with the hanging portion 65 matched to the inclined step seat 64 at the upper terminal of the drawing shaft holding cylinder 55. By this mechanism, the drawing shaft 57 is pulled out easily from the drawing shaft holding cylinder 55, and is possible to use the another kinds of pencil of the each side, and exchange the pencil easily.

The second survey line drawing means 3B is combined with the pole member 44. The second survey line drawing means 3B has the arm member 66 to be able to rotate freely attached to the pole member 44 and is arranged to adjust the position by the ups and downs adjusting screw 67. The drawing shaft holding member 69 is connected to rotate freely to the terminal side 66a of the arm member 66 through the connecting axle 68. The drawing shaft holding member 69 has, at least one, in the case of FIG. 6, two drawing shaft holding cylinder 55 (the same composition with the practical example mentioned above) vertically. The drawing shaft holding cylinder 55 is fixed to the drawing shaft holding member 69 by the cylinder ups and downs adjusting screw 70.

In the invented apparatus, the drawing shaft 57 applied to the second survey line drawing means 3B can be used the same as the first survey line drawing means 3A, and the holding mechanism of the drawing shaft 57 is also the same as mentioned above. The drawing shaft holding cylinder 55 can be used for common use or used as the temporary unification of the first survey line drawing means 3A and the second survey line drawing means 3B.

Figure 12:
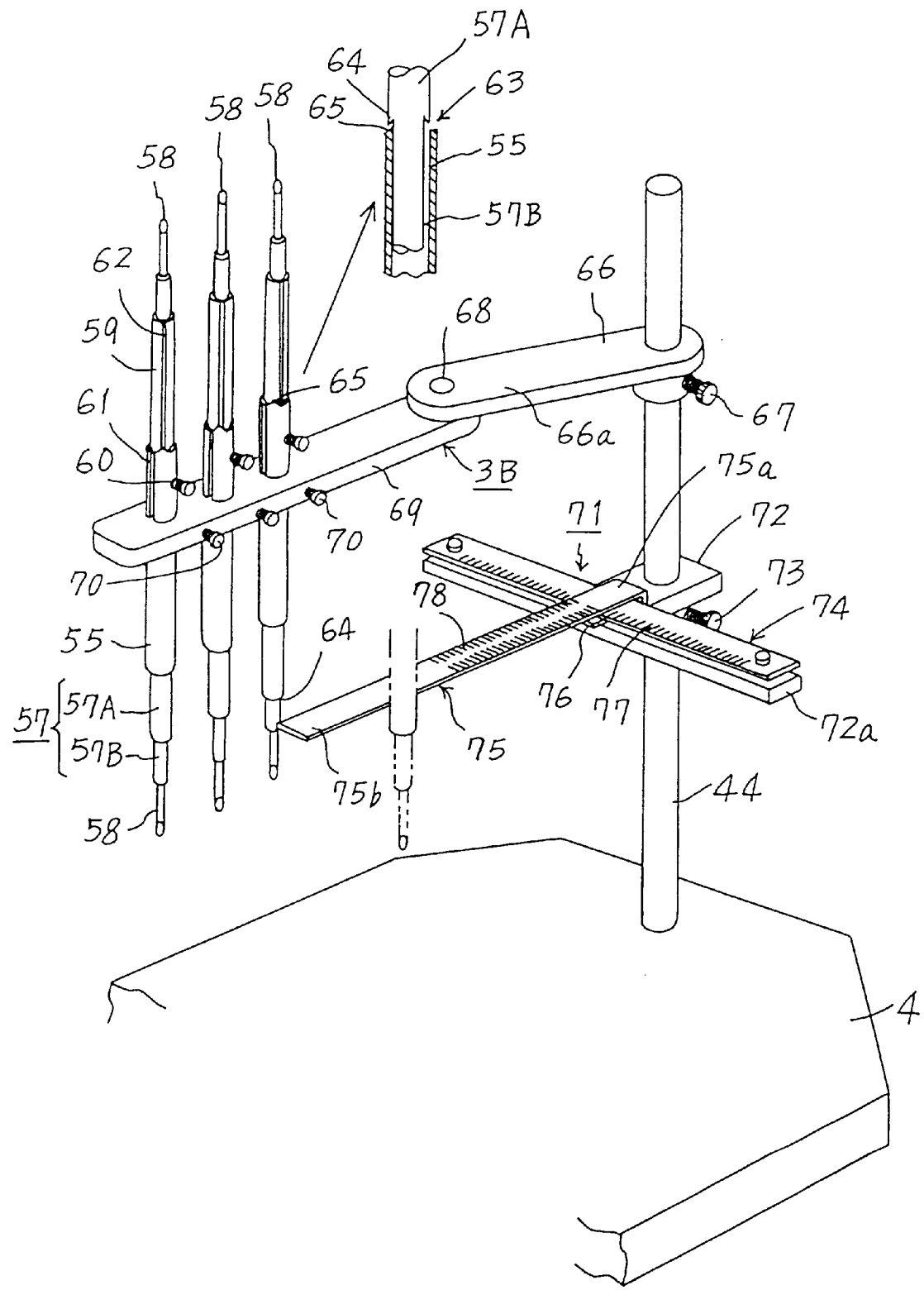
FIG. 12 is the outline of the squint view of the definite structure of the survey line drawing device which differs from that shown in FIG. 6.

Then, the another practical structure of the survey line drawing means 3 is explained in FIG. 12. This survey line drawing means 3 is composed with the second survey line drawing means 3B mentioned above and the cross gauge mechanism 71.

In this case of composition, the second survey line drawing means 3B has the arm member 66 to rotate freely attached to the pole member 44 and is arranged to adjust the position by the ups and downs adjusting screw 67. The drawing shaft holding member 69 is connected to rotate freely to the terminal side 66a of the arm member 66 through the connecting axle 68. The drawing shaft holding member 69 has, at least one, in the case shown in figure three drawing shaft holding cylinder 55 (the same composition with the practical example mentioned above) vertically. The drawing shaft holding cylinder 55 is fixed to the drawing shaft holding member 69 by the cylinder ups and downs adjusting screw 70.

On the other hand, the cross gauge mechanism 71 has the mechanism that the cross gauge supporting member 72 is attached to the pole member 44 to be able to rotate and fix by the ups and downs adjustable screw 73. The cross gauge supporting member 72 is the plate of T-shape and the first gauge 74 is attached on the top side 72a of T-shape of the cross gauge supporting member 72. The second gauge 75 has the connecting portion 76 at the one terminal 75a which crosses at right angle to the first gauge 74 and is able to move along the first gauge 74. For example, in the first gauge 74, there is the scale 77 which extends from center to the each side, and in the second gauge 75, there is the scale 78 which extends from the connecting portion 76 to the free terminal 75b.

In this invention, the pencil rod 58 of the survey line drawing means 3 is constructed to extend vertically and the dental plaster cast setting means 10 on the surveyor table 2 can rotate individually around the first axle PA-1, that is the X axis, the second axle PA-2, that is the Y axis and the third axle, that is the Z axis, and then the setting means 10 is inclined to the desired angle through the first angle adjustment mechanism 36, the second angle adjustment mechanism 37, the Z axis adjustment mechanism 11 and the universal joint mechanism 12. On this account, the inclined angle of the tooth of the dental plaster cast M on the dental plaster cast setting means 10 is roughly measured by using the round side surface of the drawing rod 58. That is to say to be able to measure roughly the inclination of the outer round side surface containing the lingual and buccal side of the tooth of the dental plaster cast M.

The surveyor apparatus with the secondary component of this invention is explained in detail with FIG. 9~FIG. 12. The surveyor apparatus with the above-mentioned first component is to draw the clasp outline based on the survey line B for the clasp and the base by using the X1-axis, the Y1-axis and the Z-axis. On the other hand, the surveyor apparatus with the secondary component is composed with the angle fine adjustment mechanism of the X2-axis and the Y2-axis adding to the X1-axis, the Y1-axis and the Z-axis.

Following, the definite component of the surveyor apparatus of the secondary component is explained. To prevent the repetition, the same part of the first component is omitted.

FIG. 9 shows roughly the figure that is to compare the surveyor of the first component with the surveyor of the secondary component and to explain each principle. FIG. 9A shows the principle of the surveyor apparatus of the first component that is composed with the combination of the Y1-axis, the X1-axis, the Z-axis, the universal joint mechanism and the dental plaster cast setting means. FIG. 9B shows the principle of the surveyor of the secondary component that is composed with the combination of the Y1-axis, the X1-axis, the Z-axis, the Y2-axis, the X2-axis, the universal joint mechanism and the dental plaster cast setting means. And FIG. 9C shows the principle of the usual surveyor apparatus with two axis component (the Y1 axis—the X1 axis—the dental plaster cast setting means).

Figure 10:
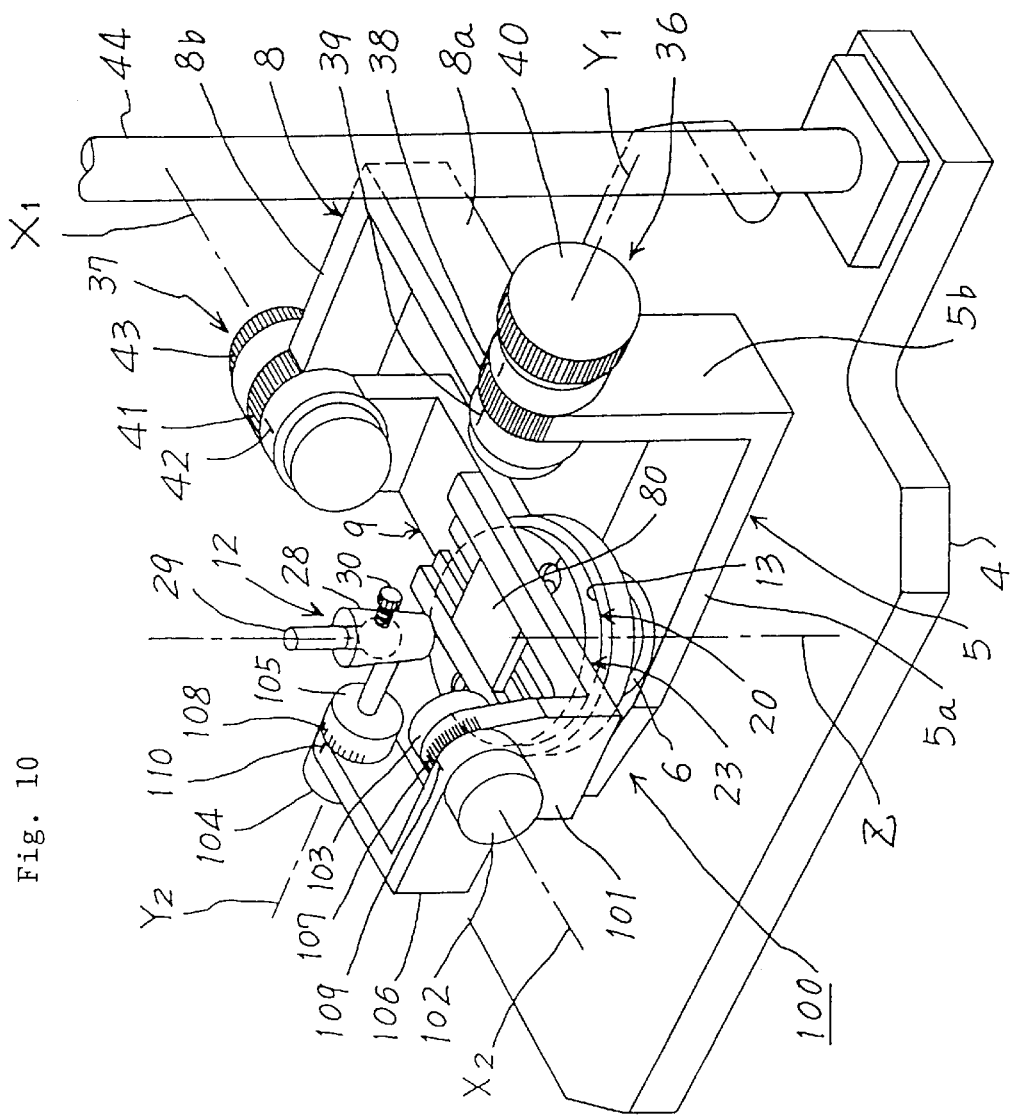
FIG. 10 shows the second structure of the surveyor apparatus for denture designing in this invention and is the outline of the squint view which shows simply the basic structure of the surveyor table.
Figure 11:
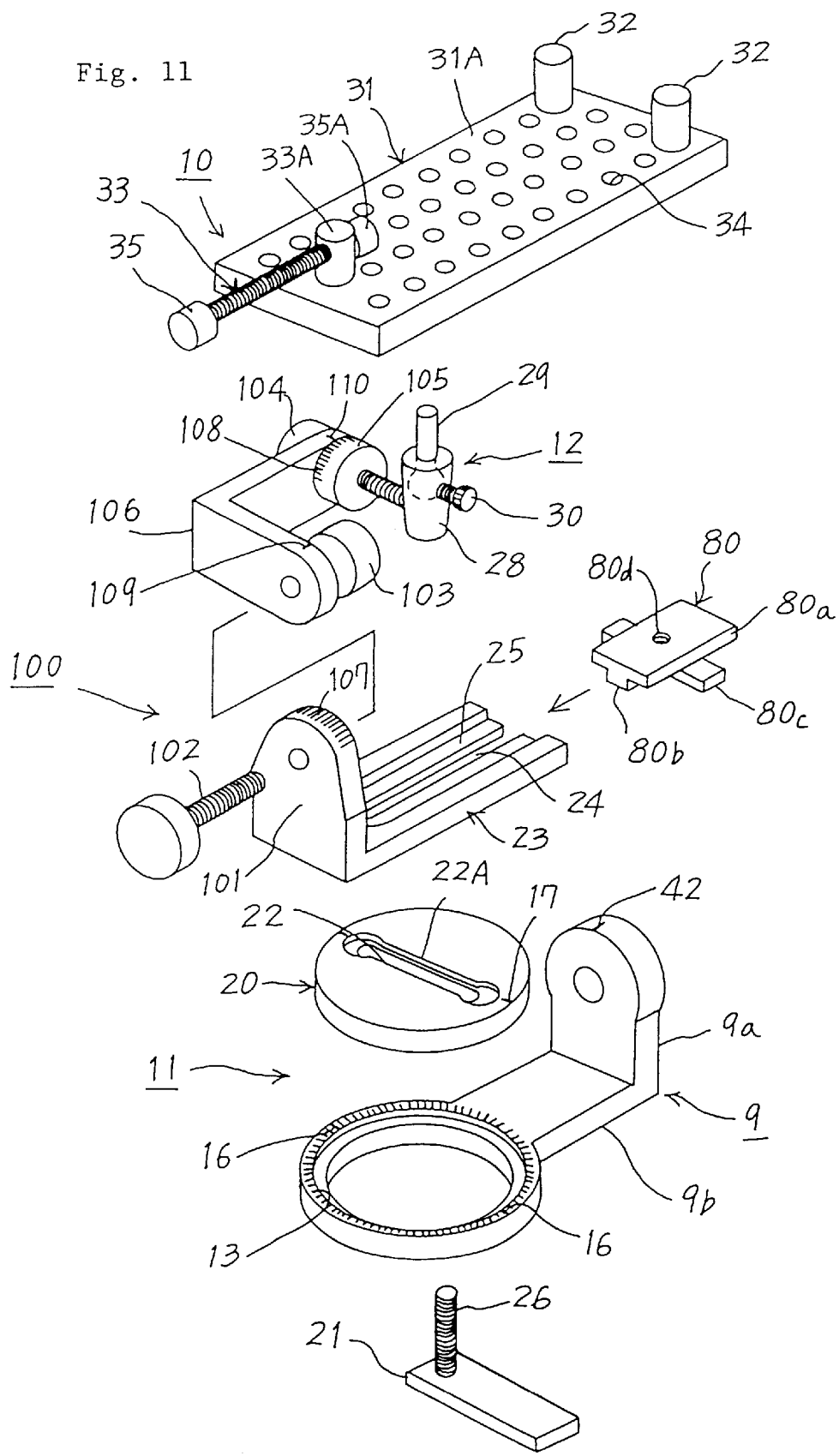
FIG. 11 is the outline of the squint view which shows to decompose the inner structure of the surveyor table of the surveyor apparatus with the second structure.

The definite example of the surveyor apparatus of the secondary component is explained with FIG. 10 and FIG. 11. The surveyor apparatus of the secondary component, showing in FIG. 11, has the structure that adds the fine angle adjustment mechanism 100 between the Z-axis adjustment mechanism 11 and the universal joint mechanism 12 of the surveyor tool of the first component.

According to the definite example shown in FIG. 11, there is the relatively large axis hole 13 at the free end terminal of the second plate part 9b in the Y-Z axis connecting arm member 9. The disk 20 with oblong hole of X(Y) axis direction is supported to be able to rotate on the axis hole 13. The scale 16 for position setting is carved on the round surface of the axis hole 13 and the reference line 17 is carved on the disk 20 with oblong hole of X(Y) axis direction. In the disk 20 with oblong hole of X(Y) axis direction, there is the oblong hole 22 extending to the diameter direction through the center of the disk and more the long groove 22A with similar figure is created in the upper surface of the oblong hole 22 of X(Y) axis direction.

On the upper side of the disk 20 with oblong hole of X(Y) axis direction, the part 23 with slit of Y(X) axis direction is arranged to be able to move each other. In the part 23 with slit of Y(X) axis direction, there is the slit 24 of Y(X) axis direction which extends straightly and is opened at one terminal, and more the long groove 25 with similar figure is arranged on the upper side of slit 24 of Y(X) axis direction.

The disk 20 with oblong hole of X(Y) axis direction and the part 23 with oblong hole of Y(X) axis direction are able to move each other and connected by the connecting slider member 80. The connecting slider member 80 is composed with the plate portion 80a which fits to be able to slide into the long groove 25 of the part 23 with slit of the Y(X) axis direction, the projected portion 80b which is on the bottom side of the plate portion 80a and fits to be able to slide into the slit 24 of Y(X) axis direction and the block portion 80c which crosses at right angle to the projected portion 80b and fits to be able to slide into the long groove 22A of the disk 20 with oblong hole of X(Y) axis direction. At the block portion 80c in the connecting slider member 80, the screw hole 80d is arranged.

On the other hand, the Z axis point fixing handle 21 to fix the Z axis point has the bolt 26. The bolt 26 is screwed into the screw hole 80d of the connecting slider member 80 through the axis hole 13 of the Y-Z axis connecting arm member 9 and the oblong hole 22 of the X(Y) axis direction in the disk 20 with oblong hole of the X(Y) axis direction, and it is fixed at the any position of the x axis and the Y axis by rotating the Z axis point fixing handle 21.

On the other hand, the dental plaster cast setting means 10 is composed with the dental plaster cast setting plate 31 which is connected on the connecting member 29 of the universal joint mechanism 12. The dental plaster cast setting plate 31 has the setting support member 32 and 33 which hold the dental plaster cast M on the upper side 31A. For example, one of the setting support member 32 is composed with the pair of pins and is fixed by inserting into the selected hole among the plural inserting hole 34 in the dental plaster cast setting plate 31. The other one of the setting support member 33 is composed with the pin 33A which is inserted selectively into the plural inserting hole 34 and the movable screw 35 which is screwed into the pin 33A, and has the cast holding part 35A at the terminal of the movable screw 35 and is arranged to hold the dental plaster cast M with the cast holding part 35A and the setting support part 32 by rotating the movable screw 35.

The fine angle adjustment mechanism 100 is composed with the X2-axis scaled bearing member 101 which is fixed to the member 23 with slit of the Y(X)-axis direction in the Z-axis adjustment mechanism 11 and the X2 axis-the Y2 axis connecting arm member 106 which is connected to make axle to the X2 axis scaled bearing member 101 with the X2 axis fixing bolt 102 and the X2 axis fixing nut 103 of the x2 axis forming means, and with Y2 axis fixing bolt 104 and the Y2 axis fixing nut 105 of the Y2 axis forming means.

In the fine angle adjustment mechanism 100, the scaled X2-axis bearing member 101 has the X2-axis angle scale 107 and the scaled Y2-axis bearing member 105 has the Y2-axis angle scale 108. On the other hand, the line of the reference of 109 and 110 to read the angle of the X2-axis and Y2-axis is marked on the X2-axis Y2-axis connecting arm member 106.

Following, the example by the surveyor apparatus with the second component is shown. The working example of the Z axis for designing of clasps is mentioned. In the former invention, from the view point of the occlausal side, the working cast is arranged to adjust one of the two axis of the X axis and the Y axis to the median line as the standard and the two rotary axis of X and Y is rotated to the desired angle and then the survey line B is drawn on the working cast for giving the outline of clasp. Especially, the side-opening design (already mentioned in the former invention) has been considered as the best designing method of the clasp designing.

But observing the tooth, especially anterior tooth and premolar (FIGS. 7A and B), there is the maximum circumference at the position of midline N of medial-distal position of the buccal and lingual surface of the tooth, and also the effective undercut area is found. It is necessary to use this area for the clasp which is aesthetic and g et the resistant force.

On the side-opening designing method in the former invention, as rotating the X axis and giving inclination, it affects for the right-angle direction (ML) against the X axis and the survey line B (the sine 83 in FIG. 7A) is drawn. It is very difficult to draw the aesthetic survey line 83', because it is necessary to adjust the angle of the X axis and the Y axis for drawing the survey line.

Then in this invention, this problem is overcomed by arranging the Z axis which rotates horizontally against the X axis and the Y axis as the axis center of cross point of the X axis and the Y axis.

Figure 7:
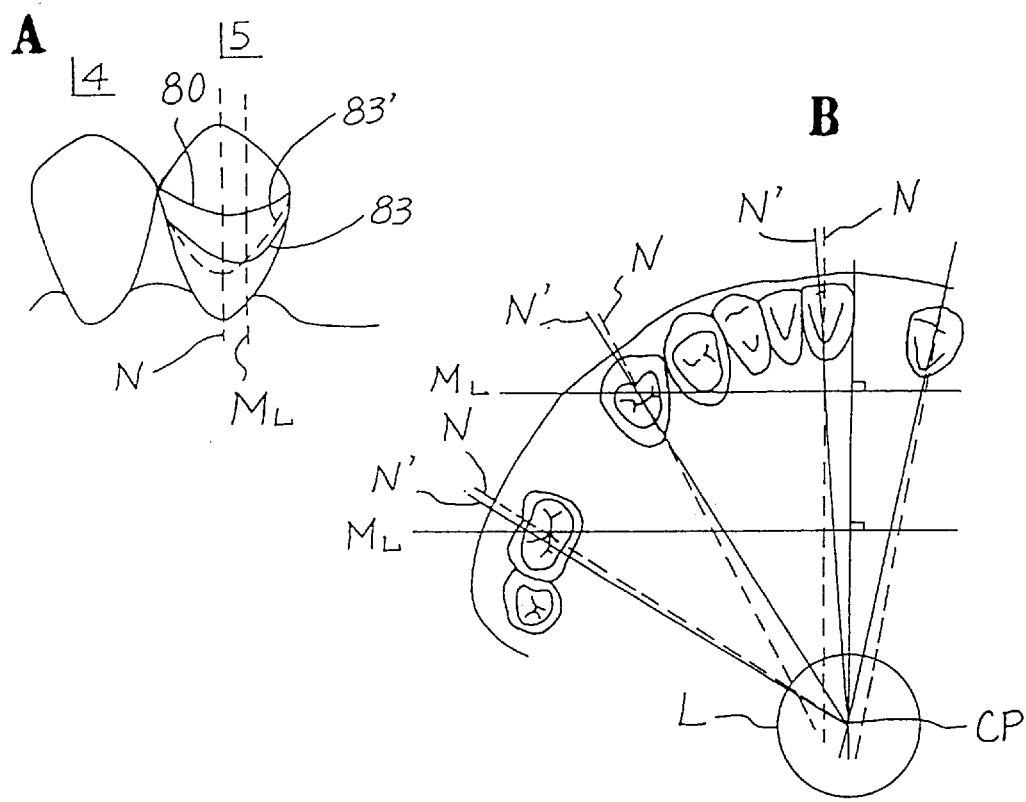
FIG. 7A is the outline of the buccal view which shows the survey line 83 and the aesthetic survey line 83' and FIG. 7B is the outline of the ground view which shows the principle to draw the survey line 83' for the side opening design with fine aesthetic.
Figure 8:
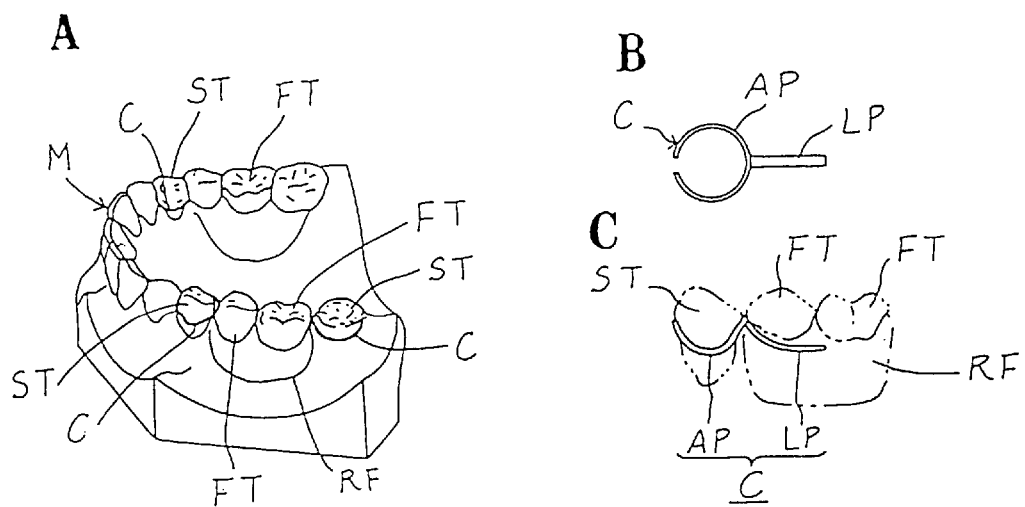
FIG. 8A is the outline of the squint view which shows the situation of the denture inserted on the dental plaster cast and FIG. 8B is the outline of the ground view which shows one example of wire-clasp and FIG. 8C is the outline of the side view which shows the situation setting the wire clasp on the dental plaster cast (shown with dotted line).

The working example of the Z axis is explained with FIG. 7 B.

As mentioned above, the aesthetic fine survey line B like a survey line 83' when each tooth is done with side-opening designing toward the center axis direction N, but it wastes too much time to design for each tooth one by one.

Then the center point (called the working origin CP) of the zone L that the line of of the direction of the center axis N for each tooth come together is adjusted to the Z rotary axis of this surveyor tool. By rotating this Z axis, the cast M is easily adjusted to the center axis N' of the clasped tooth on the X axis and the Y axis (the center axis is N, but by adjusting CP=Z, then it is designed to the N' direction). So, the aesthetic fine survey line 83' is able to draw by the side-opening design with adjusting the angle of the X axis and the Y axis.

Figure 13:
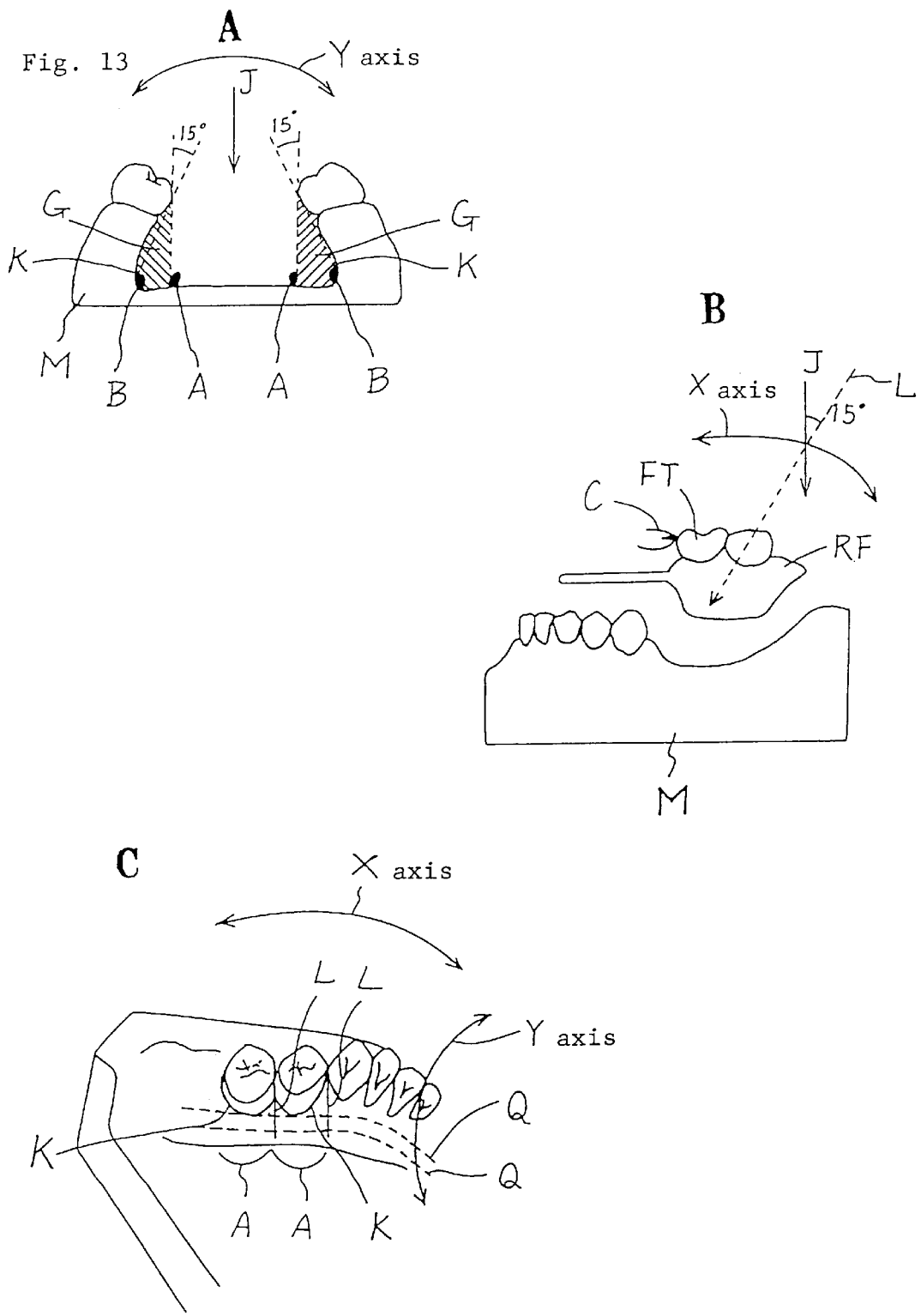
FIG. 13A, FIG. 13B and FIG. 13C is the figure that explains the lower bilateral 6 and 7 missing case with large lingual inclination.
Figure 14:
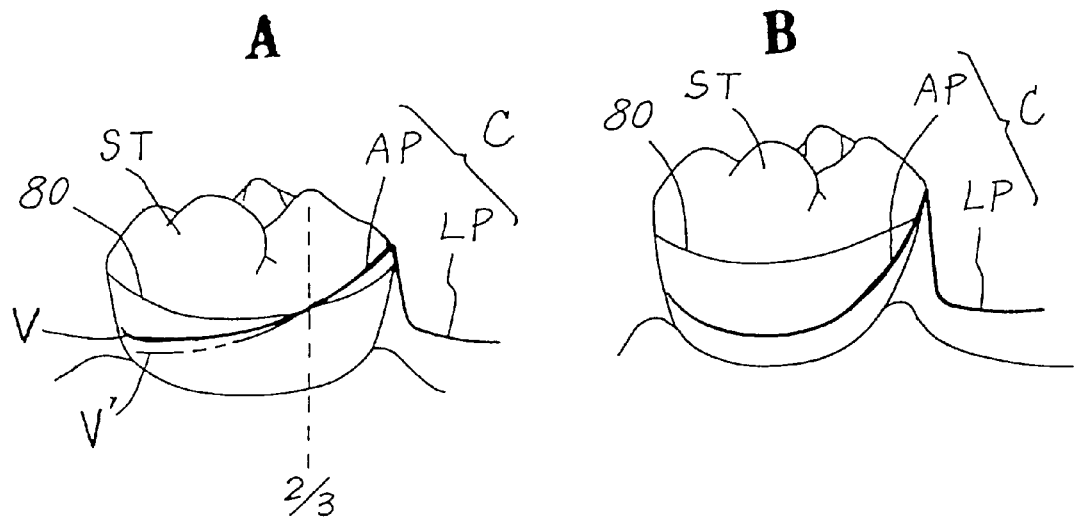
Figure 15:
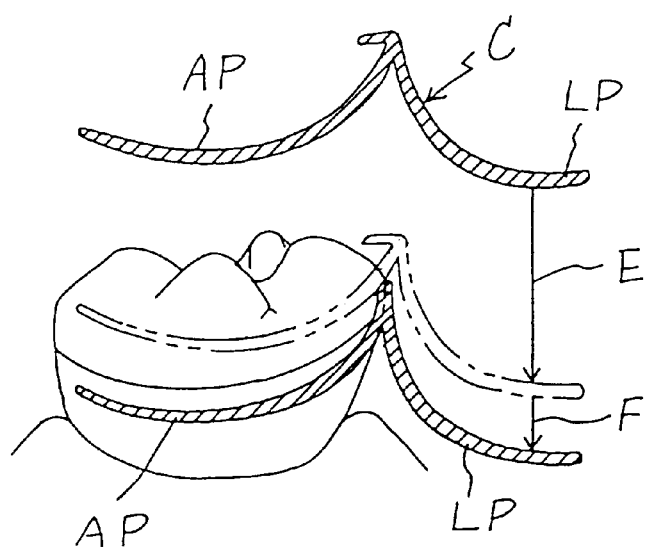
FIG. 15 is the figure which shows the relation of the designing direction E for denture base and the designing direction F for clasps.

In FIG. 13, the working example of the fine angle adjustment mechanism is explained with the case which design the wire clasps and the bar to the cast M (that lacks the lower bilateral molar 6,7 and treated with the connecting bar) and the adjacent clasped tooth (lower bilateral premolar 5) is deeply inclined to the lingual side (FIG. 13A).

As shown in FIG. 13A, it is impossible to design the bar inserting into the under-cut area when the design is made by the usual method that consider the path of insertion for only one direction, so the bar is set at the position A.

By using this inventional theory and surveyor apparatus, it enable to set the bar at the position B even for the case mentioned above. It is possible to practice the definition of this designing theory that the denture inserted for the direction of medio-distal(X-axis) inclination is able to insert into the under-cut area of the same bucco-lingual(Y-axis) inclination.

Following, the practical example is shown.

At first, the cast M is mounted on the cast table 10 after confirming all the angle setting of the X1, Y1, Z, X2 and Y2 being zero. The basic designing direction J is adjusted by the universal joint mechanism 12. Then the under-cut area of G is measured. After measuring the medio-distal (X) and the bucco-lingual(Y-axis) angle to be equal balance of right and left under-cut area, the inclination of the cast is readjusted as to the basic designing direction J by the fine angle adjustment of the universal joint mechanism, the Y2-axis and the X2-axis (It is the characteristic of this tool that this readjustment is able to do with keeping each axis of the X1, the Y1 and the Z being zero).

According to the definition of this designing method that the denture inserted to the direction of medio-distal inclination is possible to insert into the bucco-lingual under-cut area with the same angle, the direction of the insertion of the base and the direction of the bar are adjusted by considering the interference with the remaining tooth and the inference of the direction of the insertion of clasp after measuring the inclination of each axis of the medio-distal(X) and the bucco-lingual(Y) considering how much angle of bucco-lingual and medio-distal inclination is suitable for insertion (In this case, the direction of the insertion of the clasp is the same to the basic designing direction J. The direction of the insertion of the base is adjusted to the 15 degree of the distal inclination for the J direction).

Next, the drawing method of the outline of the base (the bar) is explained.

First, the survey line A is drawn with the basic designing direction J. Angle adjustment of 15 degree each of right and left is done to the Y axis, and the cast is inclined bucco-lingually (Y) and then the line k is drawn on the mucous membrane of right and left side. After that, the angle is returned to the zero. And the angle of 15 degree is given to the X axis and the cast is inclined distally to the direction of L against J, then the line L is drawn.

By these lines, the limit area to be inserted is known. So, the outline Q of the bar is drawn by hand. By this designing method, the design to insert the bar into the under-cut area is enable.

The designing of the clasps is made by the method mentioned above.

INDUSTRIAL APPLICABILITY

As the denture designing surveyor apparatus of this invention can read not only the X-axis, Y-axis and Z-axis but also the height, it is very effective to design the clasps and the denture base.

As the denture designing surveyor apparatus of this invention is composed with the simple devices, it is possible to design the clasps and the base with a simple and work-saving operation and it dissolves the defects found in the usual methods as much as possible, so this invention is very effective for making the high quality and uniform denture.

As the denture designing surveyor apparatus of this invention is possible to operate the dental plaster cast M with the three axis of X, Y and Z and to lock the established angle individually, so the dental plaster cast M is possible to rotate individually for each axis even after setting the any inclined angle, and it is very effective for the simple and work-saving drawing process of the survey line.

By the denture designing surveyor apparatus of this invention, it enable to design the clasp which has a uniform resistant force for each working force with the survey line B drawn after adjusting the proper angle for the X axis and the Y axis, so it enable to design the denture which is able to insert by rotation or multi-stage that is possible only with experiment and intuition untill now. It is also the clasp design method considering the aesthetic view or the designing method for corresponding to the delicate ups and downs of the tooth surface.

What is claimed is:

1. A surveyor apparatus for designing a denture, said surveyor apparatus comprising;

a surveyor table for setting a dental plaster cast, a survey line drawing means to draw a survey line for a denture base and clasps on said dental plaster cast, said surveyor table including, a base table, a dental plaster cast setting means which is connected to rotate individually around each axis of movement of the dental plaster cast setting means and to be fixed in position by a first axle parallel to said base table, a second axle crossed at a right angle to said first axle, a third axle positioned vertically at an intersection point of said first and second axles, a first angle-adjustment mechanism which can rotate said dental plaster cast setting means around said first axle and fix the dental plaster cast setting means to a desired angle, a second angle-adjustment mechanism which can rotate said dental plaster cast setting means around said second axle and fix the dental plaster cast setting means to a desired angle, a third angle-adjustment mechanism which can rotate said dental plaster cast setting means around said third axle and fix the dental plaster cast setting means to a desired angle, a Z axis-center adjustment mechanism which is set between said dental plaster cast setting means and said third axle and adjusts a datum point of the dental plaster cast to an axis center of said third axle, and a universal joint which is able to set a standard plane of said dental plaster cast to a desired angle against a horizontal plane.

2. A surveyor apparatus for designing a denture, said surveyor apparatus comprising;
  a surveyor table for setting a dental plaster cast, a survey line drawing means to draw the survey line for a denture base and clasps on said dental plaster cast,
  said surveyor table including,
  a base table,
  a dental plaster cast setting means which is connected to rotate individually around each axis of movement of the dental plaster cast setting means and to be fixed in position by a first axle parallel to said base table, a second axle crossed at right angle to said first axle, and a third axle positioned vertically at an intersection point of said first and second axles,
  a first angle-adjustment mechanism which can rotate said dental plaster cast setting means around said first axle and fix dental plaster cast setting means to a desired angle,
  a second angle-adjustment mechanism which can rotate said dental plaster cast setting means around said second axle and fix dental plaster cast setting means to a desired angle,
  a third angle-adjustment mechanism which can rotate said dental plaster cast setting means around said third axle and fix dental plaster cast setting means to a desired angle,
  a Z axis-center adjustment mechanism which is set between said dental plaster cast setting means and said third axle and adjusts a datum point of the dental plaster cast to the axis center of said third axle,
  a universal joint which is able to set a standard plane of said dental plaster cast to a desired angle against a horizontal plane, and
  a fine angle adjustment means which has an individual axle for said first axle and said second axle between said Z axis center adjustment mechanism and said universal joint mechanism.

3. A surveyor apparatus for the denture designing as set forth in claim 1 or claim 2, wherein said dental plaster cast setting means contains a dental plaster cast setting plate which holds and fixes said dental plaster cast, and the means to hold and to fix said dental plaster cast on said dental plaster cast setting plate is composed of a pair of fixing pins which hold one side of said dental plaster cast and a tightening means which tightens the opposite angle to hold an other side of said cast, and at least a pair of said fixing pins is able to insert into the plural pin holes made in said dental plaster cast setting plate.

4. A surveyor apparatus for the denture designing as set forth in claim 1 or claim 2, wherein said survey line drawing means is composed of a combination of the first survey line drawing device which is held by a drawing shaft working mechanism containing at least one drawing shaft extending vertically and enabling the drawing shaft to move separately toward the X-axis and the Y-axis direction and to lock independently, and a second survey line drawing means which contains at least one drawing shaft to be fixed extending along the vertical line to the desired pole through a rotable arm member.

5. A surveyor apparatus for the denture designing as set forth in claim 1 or claim 2, wherein said survey line drawing means is composed of a combination of the second survey line drawing means which contains at least one drawing shaft attached to the desired pole along the vertical line through the rotable arm, and a cross gauge mechanism which is composed of a first straight line gauge and a second straight line gauge crossing at a right angle to said first straight line gauge.

6. A surveyor apparatus for the denture designing as set forth in claim 4, wherein said survey line drawing means is composed of a holder member attached to drawing shaft working mechanism or the free end terminal of the above mentioned arm part, a cylinder member attached to said holder part, a drawing shaft supported freely through said cylinder member and a height adjustment mechanism to establish the height of said drawing shaft, and enable fixing of the drawing shaft to the drawing working position and the drawing non-working position for said cylinder member.

7. A surveyor apparatus for the denture designing as set forth in claim 5, wherein said survey line drawing means is composed of a holder member attached to drawing shaft working mechanism or the free end terminal of the above mentioned arm part, a cylinder member attached to said holder part, a drawing shaft supported freely through said cylinder member and a height adjustment mechanism to establish the height of said drawing shaft, and enable fixing of the drawing shaft to the drawing working position and the drawing non-working position for said cylinder member.

* * * * *